United States Patent [19]

Morgan et al.

[11] Patent Number: 5,397,467
[45] Date of Patent: Mar. 14, 1995

[54] LIQUID CHROMATOGRAPHY SYSTEM AND RESERVOIR CAP FOR USE THEREIN

[75] Inventors: Ned R. Morgan; John C. Bonino, both of Vineland, N.J.

[73] Assignee: Kontes Glass Company, Vineland, N.J.

[21] Appl. No.: 105,183

[22] Filed: Aug. 12, 1993

[51] Int. Cl.6 .............................................. B01D 15/08
[52] U.S. Cl. ................................. 210/198.2; 210/101; 210/656; 210/659
[58] Field of Search ............... 210/656, 659, 101, 136, 210/198.2, 257.1, 416.1

[56] References Cited

U.S. PATENT DOCUMENTS

| Re. 29,454 | 10/1977 | Ashmead | 210/198.2 |
|---|---|---|---|
| 426,756 | 4/1890 | Becker | 210/120 |
| 630,988 | 8/1899 | Reisert | 210/257.1 |
| 3,536,197 | 10/1970 | Ward | 210/120 |
| 3,800,956 | 4/1974 | Nishizawa | 210/198.2 |
| 4,077,886 | 3/1978 | Fukuda | 210/198.2 |
| 4,116,046 | 9/1978 | Stein | 210/198.2 |
| 4,311,668 | 1/1982 | Solomon | 210/198.2 |
| 4,364,263 | 2/1982 | Sankoorikal | 210/198.2 |
| 4,374,656 | 2/1983 | Schrenker et al. | 55/170 |
| 4,394,263 | 7/1983 | Dosch | 210/198.2 |
| 4,437,812 | 3/1984 | Abu-Shumays | 210/198.2 |
| 4,448,684 | 5/1984 | Paradis | 210/198.2 |
| 4,478,713 | 10/1984 | Girot | 210/198.2 |
| 4,541,452 | 9/1985 | Paradis | 210/198.2 |
| 4,595,496 | 6/1986 | Carson | 210/198.2 |
| 4,728,434 | 3/1988 | Trafford | 210/198.2 |
| 4,879,029 | 11/1989 | Whitehead | 210/198.2 |
| 4,994,180 | 2/1991 | Sims et al. | 210/198.2 |
| 5,265,642 | 11/1993 | Buckminster | 210/198.2 |
| 5,275,723 | 1/1994 | Greenley | 210/198.2 |

OTHER PUBLICATIONS

Kontes "Bioreactor & Bioseparation Products", Catalog KB 89, pp. 1–66 (1989).

*Primary Examiner*—Ernest G. Therkorn
*Attorney, Agent, or Firm*—James & Franklin; Harold James; Robert. L. Epstein

[57] ABSTRACT

A liquid chromatography system has a reservoir for the mobile phase with a cap which provides for effective control of charging the reservoir with the mobile phase, sparging the mobile phase while it is in the reservoir, feeding the mobile phase to the chromatograph, returning the mobile phase to the reservoir after it has passed through the chromatograph, venting or vacuumization of the reservoir and providing for automatic release of overpressure within the reservoir, all while maintaining the sparged environment in the reservoir.

14 Claims, 3 Drawing Sheets

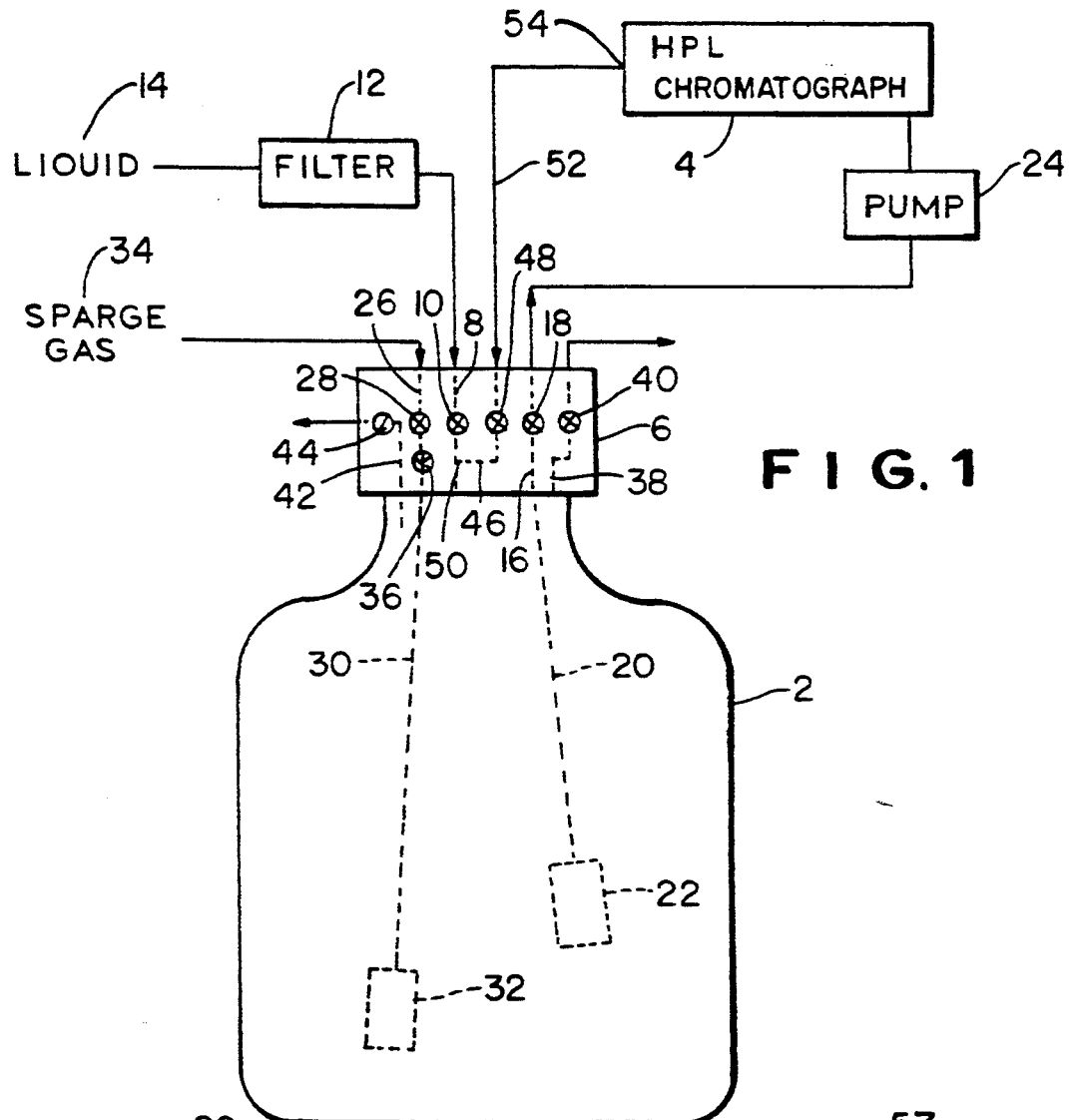
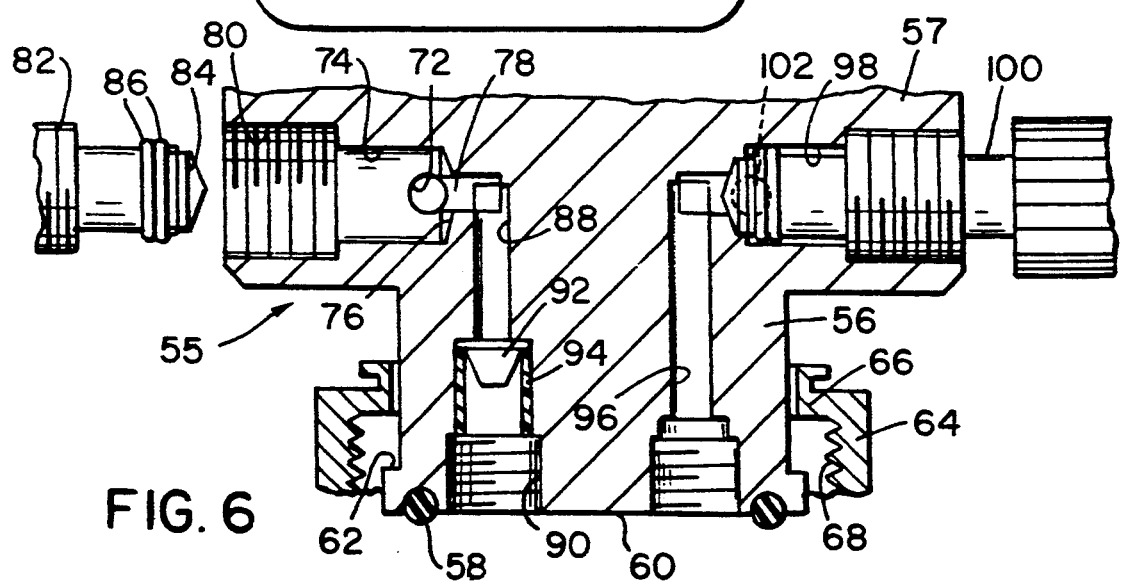

LIQUID CHROMATOGRAPHY SYSTEM AND RESERVOIR CAP FOR USE THEREIN

SUMMARY OF THE INVENTION

This invention relates to a liquid chromatography system, usually of the high pressure type, in which the mobile phase is sparged, usually with helium, and in which the usual control and maintenance functions are accomplished in the cap of the reservoir for the mobile phase used in the system and in which that mobile phase, after it has passed through the chromatograph, is returned to the reservoir through that cap, all without adversely affecting the sparging atmosphere within the reservoir.

High pressure liquid chromatography (HPLC) is a common analytical procedure. It often involves the use of a plurality of different liquids which are caused to flow through the chromatograph proper in order to assist in analyzing a particular substance. Systems of that sort therefore involve the use of a plurality of containers, one for each of the different liquids to be used. Means must be provided for charging those containers with their respective liquids while ensuring that the liquids are thus charged while they are in proper condition. In order further to ensure that the liquids used are in proper condition it is customary to subject the liquids to a process known as sparging, in which a gas, usually helium, is passed through the liquid in the container in order to remove dissolved gases from the liquid, and after the sparging operation has been completed the liquid in the container is usually blanketed with that gas under pressure in order to facilitate the feeding of the liquid from the container to the chromatograph. In order not to compromise the purity of the liquid, once it has been sparged, the sparging atmosphere must be constantly present. In a system where a plurality of such sparged containers are employed it is essential that there be no reverse flow from any given container back into the sparging system, because such reverse flow would contaminate the system and possibly the contents of the other containers. Feeding of the liquid to the chromatograph may be accomplished by a pump, but it is usually preferred that the container be pressurized, either to assist the pump or in some instances to make the pump unnecessary. The sparging medium, usually helium, is used to provide that pressure, but excessive pressure is disadvantageous and hence an automatic pressure relief valve is associated with the container. In addition, under certain circumstances it may be desired to manually vent the interior of the reservoir to the atmosphere or to apply suction to the interior of the reservoir. These functions have been carried out in the past in various ways most of which are relatively complex and many of which have been located remote from the containers themselves, thus making for relative complexity in bringing about and controlling the various operations which must be performed in order to ready the system for chromatography and to carry out that chromatography.

To perform a sparging operation is costly with respect to time and materials. The liquid which defines the mobile phase of the chromatography operation is likewise costly. In the past it has been thought that once sparging has been carried out and a sparged environment has been created in the reservoir the liquid phase, once it has passed through the chromatograph, must be discarded, to be used again only if it is subjected to a new sparging procedure. According to the present invention, however, provision is made in the chromatography system for taking the liquid phase after it has passed through the chromatograph and returning it to the previously sparged container without adversely affecting the sparged environment which has been produced. This results in a very significant saving in time and material and makes for an extremely effective chromatographic analysis. In particular, the cost of solvent purchase and disposal is greatly decreased.

Importantly, all of these operations, not only those previously carried out in such systems but also the recirculation of the mobile phase or liquid, are carried out in a controllable fashion by means provided in the removable cap to the liquid reservoir, thus centralizing all controlling operations, rendering them individually settable for each container in a system by means directly associated with that container, thus virtually eliminating the possibility of mistake in carrying out a given operation on the wrong container, and locating the controls for those operations at a given area of the cap so as not to interfere with the connections made to the cap from external sources, e.g., the liquid supply, the sparging gas supply, and the outlet to and inlet from the chromatograph.

The present invention thus produces what is believed to be the ultimate system for the preparation, delivery and conservation of isocratic HPLC mobile phases in which each mobile phase system is totally contained and airtight, for greater system reproduceability, increased system reliability and lower operating costs.

It is therefore the prime object of the present invention to devise a liquid chromatography system and a reservoir-cap combination to be used therein which optimally facilitates control of the system, and particularly of the mobile phase thereof.

It is another prime object of the present invention to devise a liquid chromatography system providing for optimum use of the mobile phase, and in particular to reuse that mobile phase by returning it to the original reservoir after it has passed through the chromatograph while retaining a fully effective sparged environment for that mobile phase.

It is yet another object of the present invention to provide a container-cap combination for use in such a system in which control of the various conditions and operations applicable to the contents of the container, including recirculation of the mobile phase, may be effected directly at the container and by means optimally located as to accessibility and effectiveness.

DESCRIPTION OF THE DRAWINGS

To the accomplishment of the above, and to such other objects as may hereinafter appear, the present invention relates to a sealed liquid chromatography system and a reservoir cap designed for use therein as defined in the appended claims and as described in this specification, taken together with the accompanying drawings in which:

FIG. 1 is a schematic view of the liquid chromatography system of the present invention, showing schematically a reservoir vessel, a sealing cap therefor, and connections thereto;

FIG. 6 is a fragmentary cross-sectional view of the cap on an enlarged scale, taken along the line 6—6 of FIG. 3.

DETAILED DESCRIPTION

Figure 2:
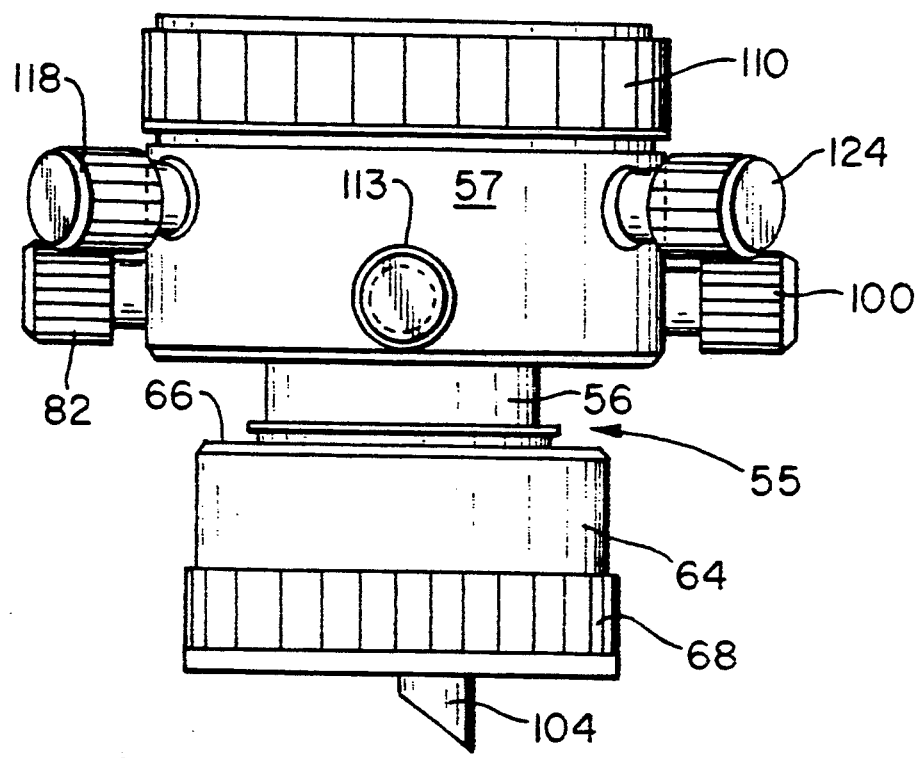
FIG. 2 is a front elevational view of a reservoir cap according to the present invention.
Figure 3:
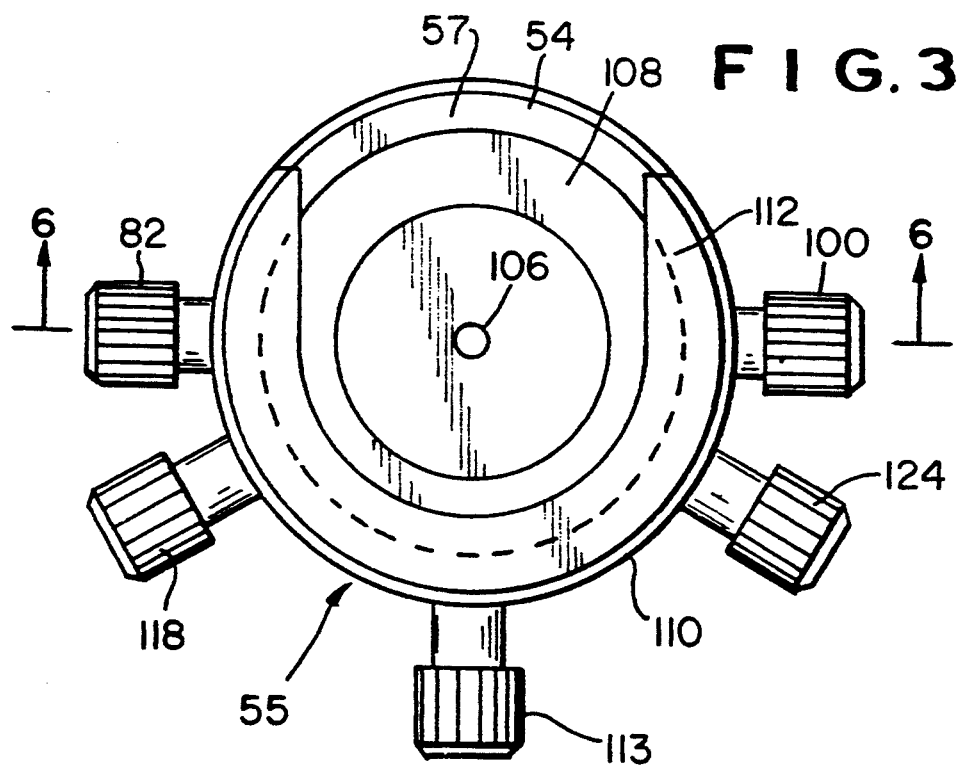
FIG. 3 is a top plan view of the cap.

Having reference first to FIG. 1, the chromatography system of the present invention utilizes as is conventional, a reservoir vessel 2 for containing the liquid which the liquid chromatograph 4, usually of the high pressure type (HPLC), uses to perform the desired procedure. That vessel 2 is provided with a cap 6, usually removable, which when in place seals the interior of the vessel 2. The cap 6 is provided with a passage 8 including an adjustable valve 10 through which passage the liquid to be used is initially brought into the vessel 2, that passage 8 therefore being externally connected, preferably by a filter 12, to a source 14 of the liquid to be used. The cap 6 is further provided with a passage 16 including adjustable valve 18 to which conduit 20 and filter 22 are connected interiorly of the vessel 2, the passage 16 being connected exteriorly to pump 24 which when energized removes liquid from the vessel 2 and supplies it to the chromatograph 4, usually at an elevated pressure. It is conventional to provide a gas such as helium under pressure, e.g. 3 psi, to the liquid contents of the vessel 2 for sparging purposes, that is to say, the removal of dissolved gases from the liquid prior to use with the chromatograph 4, and to then blanket the liquid in the vessel 2 with helium or other appropriate gas under relatively low pressure. To that end the cap 6 is provided with a passage 26 including adjustable valve 28 connected exteriorly to a source 34 of sparging gas. Because the pressure within the vessel 2 sometimes is greater than the pressure in the exterior connection to passage 26 there is a tendency, particularly when a plurality of vessels 2 are connected to a common source or manifold, for liquid from a given vessel 2 to be drawn up from the vessel 2 and toward the sparging gas source 34, with the consequent danger of contaminating the entire system externally of the particular vessel 2. Hence the cap 6 includes, as part of the passage 26, a check valve 36 permitting liquid flow into the vessel 2 but preventing liquid flow in the opposite direction, e.g. when the pressure on the supply side falls to less than 1 psi.

The cap 6 is further provided with passage 38 including adjustable valve 40 which extends between the interior of the vessel 2 and the exterior of the cap 6, the passage 38 thus being usable either to vent the interior of the vessel 2 to atmosphere or to be connected to a suitable vacuum source when vacuumization of the interior of the vessel 2 is desired. In addition, because when in use the interior of the vessel 2 is pressurized and in order to guard against any damage to the system if that pressure becomes excessive, the cap 6 is provided with a passage 42 communicating between the interior of the vessel 2 and the exterior of the cap 6, that passage including a pressure relief valve 44 set to vent at, e.g., 5 psi. The passages thus far described perform functions that have previously been performed in the chromatography system of the type under discussion, but by means of structure and system arrangements of appreciable complexity. By incorporating performance of all of these functions in the vessel cap 6 the resulting system is greatly simplified and control and adjustment of the several functions by the operator of the system is greatly facilitated.

In addition, the cap 6 is provided with a passage 46 having its own adjustable valve 48 and communicating between the exterior of the cap 6 and the interior of the vessel 2, preferably by joining the liquid passage 8 at point 50 between the adjustable valve 10 of the passage 8 and the interior of the vessel 2. The exterior end of the passage 46 is adapted to be connected by the closed line 52 in FIG. 1 to the output 54 of the chromatograph 4, thus permitting the recirculation of an isocratic HPLC mobile phase stream from the HPLC system detector back into the reservoir vessel 2 for the HPLC mobile phase while maintaining a closed loop helium-sparged (de-gassed) and pressurized environment.

FIGS. 2–6 disclose a preferred embodiment of the cap 6 schematically shown in FIG. 1. That cap comprises a body generally designated 55 having an upper portion 57 of relatively large diameter and a lower portion 56 of smaller diameter, the latter being designed to seat on the top rim of the vessel 2 and to engage that rim by means of sealing ring 58 carried in the lower surface 60 of the bottom portion 56. An upwardly facing ledge 62 is formed adjacent the lower end of the body portion 56, and a screw clamp ring 64 is captively rotatably mounted on that lower body portion 56, the ring 64 having an upper inwardly directed portion 66 designed to seat on the ledge 62 and having an internally threaded depending portion 68 designed to engage with the external threads on the neck of the vessel 2, so that when the clamp 64 is screwed down onto the neck of the vessel 2 the body 52 is secured to the open top of the vessel 2 and seals that top.

The upper and lower body portions 57 and 56 are provided with internal passages and with valves to produce the passage and valve system disclosed in FIG. 1. To that end the passage 26 in the cap 6 for the sparging gas begins at opening 70 in the side surface of the body portion 57, that opening being countersunk so as to sealably receive the end of tubing for the sparging gas. The opening 70 communicates with the passage 72 one end of which is shown in FIG. 6 and which opens into a large cavity 74 the innermost portion 76 of which is tapered and communicates with passage 78 and the outermost portion 80 of which is internally threaded and is designed to receive an externally threaded valve stem 83 having a tip 84 carrying sealing rings 86 and designed to be received in the cavity 74 to produce a helium-tight seal and controllably restrict access to the passage 78. The passage 78 in turn communicates with passage 88 which in turn communicates with slightly enlarged passage 90 which opens onto the interior of the vessel 2. Housed within the passage 90 is a duckbill type check valve 92 held in place by a press fitted Teflon or other suitable plastic sleeve 94, the duckbill valve 92 corresponding to the check valve 36 of FIG. 1. The valve stem 82 and associated structure corresponds to the adjustable valve 28 of FIG. 1.

The pump feeding passage 16 and valve 18 of FIG. 1 are constituted by the upwardly extending passage 96 shown in FIG. 6 the lowermost end of which is countersunk so as to receive the conduit 20, the passage 96 communicating with a cavity 98 in which valve stem 100 is threadedly received, that cavity 98 in turn communicating with passage 102 which extends to the countersunk opening 104 in the side surface of the upper body part 54 for receiving connecting tubing. Threading of the valve stem 100 into and out of the cavity 98 controls flow through the passage 16, thus corresponding to the valve 18 of FIG. 1.

Similar internal passages, cavities and valve stems make up the other passages through the cap 6 shown in FIG. 1. The liquid passage 8 starts with a tubular drip tip 104 which depends from the lower surface 60 of the bottom cap portion 56 and it ends at opening 106 centrally located at the upper surface of the body portion 54, where it is surrounded by an elevated flat surface 108 designed to receive an appropriate filter 12. By thus filtering directly into the reservoir 2 transfer of the mobile phase, with the attendant risk of particle contamination, is eliminated. The outer surface of the uppermost portion of the cap is externally threaded and threadedly receives thereon a screw clamp ring 110 having an upper radially inwardly extending approximately semi-circular flange 112, thereby to secure in place on the top of the cap 6 the filter 12 and the fitting, e.g. a solvent pickup adapter, which communicates with the liquid supply source 14. Valve stem 113 adjustably controls the valve 10 of FIG. 1.

The vent/vacuum passage 38 and associated valve 40 are constituted in the cap here disclosed by opening 114 in the lower surface of the cap which communicates with countersunk tube-receiving opening 116 in the side surface of the cap by means of a cavity with which valve stem 118 cooperates to control valve 40. The pressure relief valve 44 is mounted in the side of the body portion 57 and communicates with opening 120 in the bottom surface of the cap. The recirculation passage 46 extends from countersunk tubing-receiving opening 122 on the side surface of the cap 6 to the point 50 on passage 8 via a cavity with which valve stem 124 cooperates to control valve 48 of FIG. 1.

Figure 4:
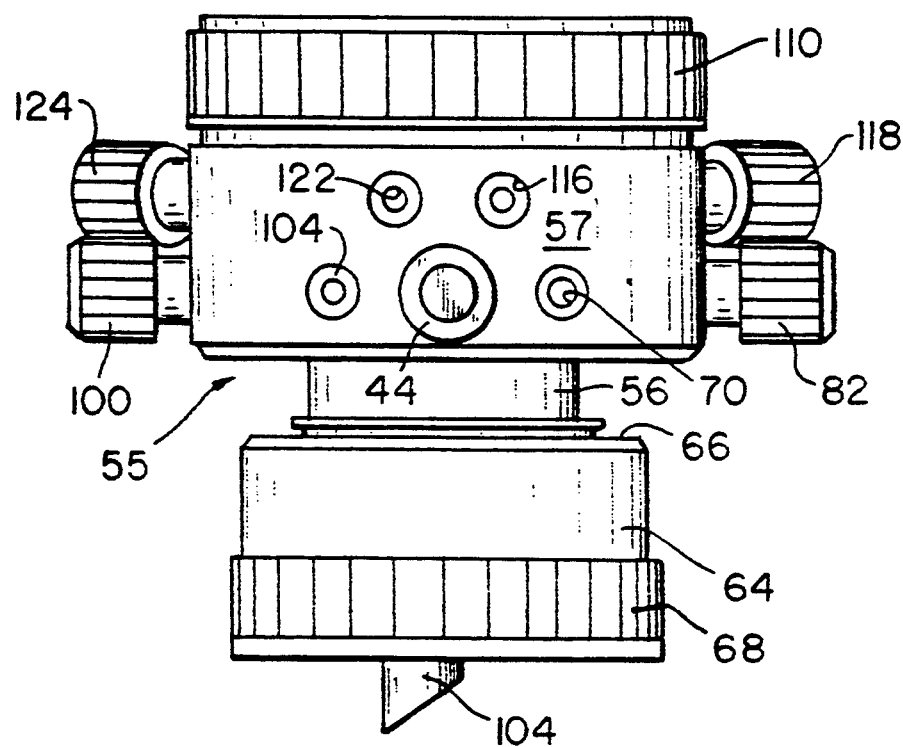
FIG. 4 is a rear view of the cap.
Figure 5:
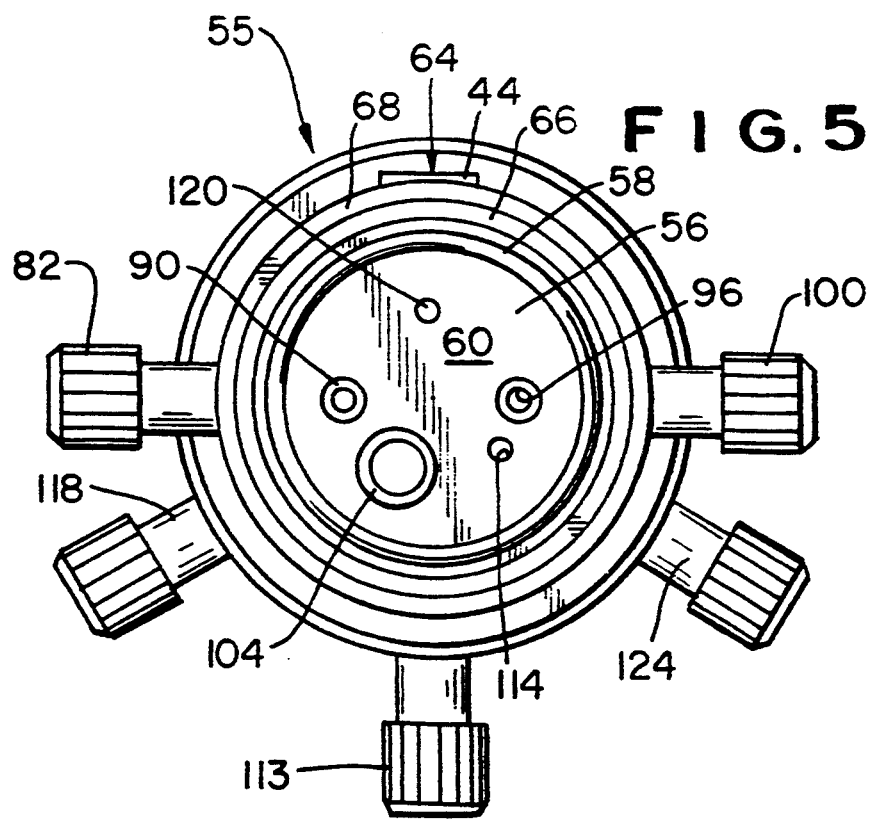
FIG. 5 is a bottom view of the cap.

It will be noted, particularly by a comparison of FIGS. 2 and 4, that the openings 70, 104, 116 and 122 for receiving external tubing are grouped together over a limited portion of the area of the side surface of the cap 6, while the valve stems 82, 100, 113, 118 and 124 are grouped together over a different limited side surface area. This reduces the typical "spaghetti" clutter of tubing at the reservoir, facilitates access to the function-controlling valve stems, and ensures that operation of one or more valve stems will not dislodge any tubing in those openings, thus facilitating operation of the system while minimizing any possibility of system dislocation.

As a result, each individual reservoir 2 utilized in the system can be independently controlled with respect to all of the operations and functions in which it may participate. The liquid in the reservoir 2 comprising the mobile phase of the chromatography system is fed into the reservoir through an appropriate filter, sparging of the mobile phase and blanketing thereof is accomplished, the interior of the reservoir can be vented or vacuumized as required, reverse flow from the reservoir back into the system is prevented, excess pressure if it develops is automatically vented, the mobile phase is fed to the chromatograph, and the mobile phase is returned from the chromatograph to the reservoir, each of those operations being individually controllable for each reservoir through manipulation of readily accessible elements, all of those functions for a given reservoir being performed and controlled by elements of the cap for that reservoir, and all of those functions being carried out without adversely affecting the sparged environment in the reservoir once that environment is produced. Hence system reproduceability and reliability are achieved at a low cost, and with each reservoir individually controllable independently of any other reservoirs which may be associated with it in the system.

While but a single embodiment of the present invention has been here disclosed, it will be apparent that many variations may be made therein, all within the spirit of the invention as defined in the following claims.

We claim:

1. A sealed liquid chromatography system comprising a liquid chromatograph, a vessel for solvent to be used in said system, first means operatively connected to said vessel for controllably sparging said solvent, second means operatively connected to said vessel for feeding said solvent from said vessel to said chromatograph, and third means operatively connected to said vessel and to said chromatograph for returning said solvent to said vessel after it has passed through said chromatograph, said second and third means and said vessel defining, in conjunction with said chromatograph, a sealed system for said solvent.

2. In the system of claim 1, means operatively connected to said vessel for feeding liquid to said vessel.

3. The system of either of claims 1 or 2, in which each of said means comprises an individually adjustable valve.

4. The system of either of claims 1 or 2, in which said vessel has an open top and is provided with a top closure sealably engaging said open top, each of said means comprising a passage through said closure.

5. The system of claim 4, in which said closure also comprises valve and passage means for adjustably venting the interior of said vessel to the exterior of said vessel.

6. The system of claim 4, in which said sparging means comprises a check valve carried by said closure and effective to permit fluid flow only into said vessel.

7. The system of either of claims 1 or 2, in which said vessel is provided with a top closure, each of said means comprising a passage through said closure and an individually adjustable valve carried by said closure.

8. The system of claim 7, in which said closure also comprises valve and passage means for adjustably venting the interior of said vessel to the exterior of said vessel.

9. The system of claim 7, in which said sparging means comprises a check valve carried by said closure and effective to permit fluid flow only into said vessel.

10. The system of claim 1, in which said cap has an outer surface and each of said means comprises an inlet opening and a valve in said cap having an externally accessible adjusting member, said inlet openings of said means being located within one area of said outer surface and said adjusting members of said valves being located within a different area of said outer surface.

11. The system of claim 10, in which said outer surface of said cap comprises a top surface and a side surface, both of said areas being on said side surface.

12. In the system of claim 10, means operatively connected to said vessel for feeding liquid to said vessel.

13. The system of claim 12, in which said means for feeding liquid comprises an inlet opening and a valve in said cap having an externally accessible adjustable member, said outer surface of said cap comprising a top surface and a side surface, said inlet opening of said liquid feeding means being located on said top surface and said adjustable member for the valve of said liquid feeding means being located within said different area, said different area being on said side surface of said cap.

14. The system of claim 13, in which said one area is on said side surface of said cap.

* * * * *